US006586189B2

(12) United States Patent
Forman (10) Patent No.: US 6,586,189 B2
(45) Date of Patent: Jul. 1, 2003

(54) SCREENING METHOD FOR PPAR-γ LIGANDS

(75) Inventor: Barry Forman, Newport Beach, CA (US)

(73) Assignee: City of Hope, Durarte, CA (US)

( * ) Notice: Subject to any disclaimer, the term of this patent is extended or adjusted under 35 U.S.C. 154(b) by 0 days.

(21) Appl. No.: 09/778,034

(22) Filed: Feb. 7, 2001

(65) Prior Publication Data

US 2001/0032338 A1 Oct. 18, 2001

Related U.S. Application Data

(63) Continuation-in-part of application No. 09/596,083, filed on Jun. 16, 2000.
(60) Provisional application No. 60/139,718, filed on Jun. 18, 1999.

(51) Int. Cl.$^7$ ............................ G01N 33/53; C07K 1/00
(52) U.S. Cl. ........................................ 435/7.1; 530/350
(58) Field of Search ...................... 435/6, 7.1, 7.21, 435/455, 320.1; 530/350

(56) References Cited

U.S. PATENT DOCUMENTS

| 4,981,784 | A | 1/1991 | Evans et al. ............... 435/6 |
|---|---|---|---|
| 5,071,773 | A | 12/1991 | Evans et al. ............. 436/501 |
| 5,217,867 | A | 6/1993 | Evans et al. ............. 435/7.1 |
| 5,571,696 | A | 11/1996 | Evans et al. ............ 435/69.1 |
| 5,597,693 | A | 1/1997 | Evans et al. ............... 435/6 |
| 5,702,914 | A | 12/1997 | Evans et al. ............. 535/29 |
| 5,710,004 | A | 1/1998 | Evans et al. ............... 435/6 |
| 5,736,157 | A | 4/1998 | Williams ................. 424/450 |
| 5,906,920 | A | 5/1999 | Evans et al. ............. 435/7.1 |
| 5,990,163 | A | 11/1999 | Evans et al. ............. 514/549 |
| 6,248,520 | B1 * | 6/2001 | Roeder et al. ............... 435/6 |
| 6,365,361 | B1 * | 4/2002 | Taniguchi et al. ......... 435/7.2 |

FOREIGN PATENT DOCUMENTS

| WO | WO 94/18346 | 8/1994 |
|---|---|---|
| WO | WO 97/35195 | 9/1997 |
| WO | WO 00/01820 | * 1/2000 |

OTHER PUBLICATIONS

Zhu et al., Isolation and characterization of PBP, a protein that interacts with peroxisome proliferator–activated receptor, 1997, The Journal of Biological Chemistry, vol. 272, pp. 25500–25506.*

Apfel, R., et al., "A Novel Orphan Receptor Specific for a Subset of Thyroid Hormone–Responsive Elements and Its Interaction with the Retinoid/Thyroid Hormone Receptor Subfamily," *Molecular and Cellular Biology*, Oct. 1994, pp. 7025–7035.

Blanco, J.C.G., et al., "The histone acetylase PCAF is a nuclear receptor coactivator," *Genes and Development* 12:1638–1651, 1998.

Blumberg, B., et al., "BXR, an embryonic orphan nuclear receptor activated by a novel class of endogenous benzoate metabolites," *Genes and Development* 12:1269–1277, 1998.

Blumberg, B., et al., "Orphan nuclear receptors—new ligands and new possibilities," *Genes and Development* 12:3149–3155, 1998.

Brown, M.S., et al., "The SREBP Pathway: Regulation of Cholesterol Metabolism by Proteolysis of a Membrane–Bound Transcription Factor," *Cell*, vol. 89, pp. 331–340, May 2, 1997.

Glass, C.K., et al., "Nuclear receptor coactivators," *Current Opinion in Cell Biology*, 9:222–232, 1997.

Fondell, J.D., et al., "Thyroid hormone receptor–associated proteins and general positive cofactors mediate thyroid hormone receptor function in the absence of the TATA box–binding protein–associated factors of TFIID," *Proc. Natl. Acad. Sci. USA*, vol. 96, pp. 1959–1964, Mar. 1999.

Forman, B.M., et al., "15 Deoxy–$\Delta^{12,\,14}$–Prostaglandin J$_2$ Is a Ligand for the Adipocyte Determination Factor PPAR$_\gamma$," *Cell*, vol. 83, pp. 803–812, Dec. 1, 1995.

Forman, B.M., et al., "Hypolipidemic drugs, polyunsaturated fatty acids, and eicosanoids are ligands for peroxisome proliferator–activated receptors α and δ," *Proc. Natl. Acad.. Sci.. USA*, vol. 94, pp. 4312–4317, Apr. 1997.

Forman, B.M., et al., "Identification of a Nuclear Receptor That Is Activated by Farnesol Metabolites," *Cell*, vol. 81, pp. 667–693, Jun. 2, 1995.

Forman, B.M., et al., "The orphan nuclear receptor LXRα is positively and negatively regulated by distinct products of mevalonate metabolism," *Proc. Natl. Acad.. Sci.. USA*, vol. 94, pp. 10588–10593, Sep. 1997.

Hong, H., et al., "GRIP–1, a novel mouse protein that serves as a transcriptional coactivator in yeast for the hormone binding domains of steroid receptors," *Proc. Natl. Acad. Sci. USA*, vol. 93, pp. 4948–4952, May 1996.

Janowski, B.A., et al., "An oxysterol signalling pathway mediated by the nuclear receptor LXRα," *Nature*, vol. 383:728–731, Oct. 24, 1996.

Kliewer, S.A., et al., "An Orphan Nuclear Receptor Activated by Pregnanes Defines a Novel Steroid Signaling Pathway," *Cell*, vol. 92, pp. 73–82, Jan. 9, 1998.

Krey, G., et al., "Fatty Acids, Eicosanoids, and Hypolipidemic Agents Identified as Ligands of Peroxisome Proliferator–Activated Receptors by Coactivator–Dependent Receptor Ligand Assay," *Molecular Endocrinology*, vol. 11, No. 6, pp. 779–791, 1997.

(List continued on next page.)

*Primary Examiner*—David Guzo
*Assistant Examiner*—Quang Nguyen
(74) *Attorney, Agent, or Firm*—Rothwell, Figg, Ernst & Manbeck (57) ABSTRACT

The invention relates to a method of identifying nuclear receptor controlled genes in specific tissues. In particular, the method also provides a method of activating PPARγ nuclear receptor controlled target genes in vivo in a tissue-specific manner and screening for PPARγ ligands.

3 Claims, 6 Drawing Sheets

OTHER PUBLICATIONS

Lehmann, J.M., et al., "Activation of the Nuclear Receptor LXR by Oxysterols Defines New Hormone Response Pathway," *The Journal of Biological Chemistry*, vol. 272, No. 6, Feb. 7, 1997, pp. 3137–3140.

Mangelsdorf, D.J., et al., "The RXR Heterodimers and Orphan Receptors," *Cell*, vol. 83, pp. 841–850, Dec. 15, 1995.

Perlmann, T., et al., "Determinants for selective RAR and TR recognition of direct repeat HREs," *Genes and Development* 7:1411–1422, 1993.

Rachez, C., et al., "Ligand–dependent transcription activation by nuclear receptors requires the DRIP complex," *Nature*, vol. 398, pp. 824–828, Apr. 29, 1999.

Spiegelman, B.M., et al., "Adipogenesis and Obesity: Rounding Out the Big Picture," *Cell*, vol. 87, pp. 337–389, Nov. 1, 1996.

Takeyama, K., et al., "Selective Interaction of Vitamin D Receptor with Transcriptional Coactivators by a Vitamin D Analog," *Molecular and Cellular Biology*, pp. 1049–1055, Feb. 1999.

Taniguchi, T., et al., "Regulation of Cholesterol 7 α–Hydroxylase Gene Expression in Hep–G2 Cells—Effect of Serum, Bile Salts and Coordinate and Noncoordinate Regulation with Other Sterol–Responsive Genes," *The Journal of Biological Chemistry*, vol. 269, No. 13, pp. 10071–10078, Apr. 1, 1994.

Twisk, J., et al., "Suppression of sterol 27–hydroxylase mRNA and transcriptional activity by bile acids in cultured rat hepatocytes," *Biochem. J.*, pp. 505–511, 1995, vol. 305.

Umesono, K., et al., "Direct Repeats as Selective Response Elements for the Thyroid Hormone, Retinoic Acid, and Vitamin $D_3$ Receptors," *Cell*, vol. 65, pp. 1255–1266, Jun. 28, 1991.

Wang, H., et al., "Endogenous Bile Acids Are Ligands for the Nuclear Receptor FXR/BAR," *Molecular Cell*, vol. 3, pp. 543–553, May 1999.

Willy, P., et al., "LXR, a nuclear receptor that defines a distinct retinoid response pathway," *Genes & Development* 9:1033–1045, 1995.

Willson, T.M. et al., "The Structure–Activity Relationship between Peroxisome Proliferator–Activated Receptor γ Agonism and the Antihyperglycemic Activity of Thiazolidinediones," *J. Med. Chem.*, pp. 665–668, 1996, vol. 39, No. 3.

"Closing the Loop on Cholesterol," *Science*, vol. 284, p. 1235, May 21, 1999.

Sadowski, I., et al., "A vector for expressing GAL4(1–147) fusions in mammalian cells," *Nucleic Acids Research*, vol. 17, No. 18, p. 7539, 1989.

Weinberger, C., "A Model for Farnesoid Feedback Control in the Mevalonate Pathway," *TEM*, vol. 7, No. 1, p. 1–6, 1996.

\* cited by examiner

SEQUENCE LISTING

<160> NUMBER OF SEQ ID NOS: 2

<210> SEQ ID NO 1
<211> LENGTH: 16
<212> TYPE: DNA
<213> ORGANISM: mammalian
<220> FEATURE:
<221> NAME/KEY: misc_feature
<222> LOCATION: (1)..(1)
<223> OTHER INFORMATION: n = any nucleotide base
<221> NAME/KEY: misc_feature
<222> LOCATION: (2)..(2)
<223> OTHER INFORMATION: n = any nucleotide base
<221> NAME/KEY: misc_feature
<222> LOCATION: (3)..(3)
<223> OTHER INFORMATION: n = any nucleotide base
<221> NAME/KEY: misc_feature
<222> LOCATION: (10)..(10)
<223> OTHER INFORMATION: n = any nucleotide base

<400> SEQUENCE: 1
nnnaggtcan aggtca                                                        16

<210> SEQ ID NO 2
<211> LENGTH: 6
<212> TYPE: DNA
<213> ORGANISM: mammalian

<400> SEQUENCE: 2 aggtca                                                                    6

SCREENING METHOD FOR PPAR-γ LIGANDS

CROSS REFERENCE TO RELATED APPLICATIONS

This application is a continuation-in-part of copending prior application Ser. No. 09/596,083, filed Jun. 16, 2000, which claims priority from copending provisional application Serial No. 60/139,718, filed Jun. 18, 1999.

BACKGROUND OF THE INVENTION

1. Technical Field

This application relates to a method of activating PPARγ nuclear receptor controlled target genes in vivo and screening for PPARγ ligands.

2. Background of the Invention

The thiazolidinedione class of antidiabetic drugs represent one of the few treatments of diabetes that alleviate insulin resistance, hyperglycemia and hyperlipidemia in patients with NIDDM. Thiazolidinediones are ligands for peroxisome proliferator activated receptor-γ (PPARγ), a member of the nuclear receptor superfamily. This molecular linkage implies that thiazolidinediones achieve their insulin resistance effects by regulating PPARγ target genes. However, the precise pathway connecting PPARγ activation to insulin sensitization remains a mystery.

The peroxisome proliferator activated receptor γ (PPARγ, Unigene # Hs. 100724) is a nuclear receptor that regulates gene transcription in response to lipid-like ligands including 15-deoxy-$\Delta^{12,14}$ $PGJ_2$, thiazolidinediones and other related analogs. PPARγ ligands have principally been used clinically for the treatment of hyperlipidemia and non-insulin resistant diabetes (NIDMM) but have been implicated for potential treatment of other diseases including obesity, colon cancer, psoriasis, inflammatory bowel disease, polycystic ovary disease, cancer (including liposarcoma, breast cancer, prostate cancer) and cardiovascular disease (including atherosclerosis, foam cell formation and endothelial cell dysfunction). Thus, the identification of PPARγ ligands has important clinical implications. In particular, the target tissue for PPARγ action is unknown. Therefore, it is unclear which PPARγ target genes contribute to the normalization of insulin response.

Transgenic mice have been developed that express a constitutively active form of PPARγ in either brown fat, white fat, skeletal muscle or liver. Each mouse line will be evaluated for parameters of insulin responsiveness under normal and diabetogenic conditions. This will allow us to determine whether activation of PPARγ target genes in any one (or combination) of tissue(s) is sufficient to relieve insulin resistance in vivo.

Molecular cloning studies have demonstrated that nuclear receptors for steroid, retinoid, vitamin D and thyroid hormones comprise a superfamily of regulatory proteins that are structurally and functionally related. Nuclear receptors contain a central DNA binding domain that binds to cis-acting elements (response elements) in the promoters of their target genes. Once bound to a response element, nuclear receptors activate transcription of specific genes through their conserved C-terminal ligand binding domains which bind hormones with high affinity and specificity. The ligand binding domain is a complex entity containing several embedded subdomains. These include a C-terminal transactivation function and a dimerization interface. Binding of the specific ligands to the nuclear receptor results in a conformation change that promotes interactions between the transactivation domain and several transcriptional co-activator complexes. These complexes destabilize chromatin and activate transcription. Through this mechanism, nuclear receptors directly regulate transcription in response to their specific ligands.

An important advance in the characterization of this superfamily of regulatory proteins has been the discovery of a growing number of gene products which possess the structural features of hormone receptors but which lack known ligands. These are known as orphan receptors, which like the classical members of the nuclear receptor superfamily, possess DNA and ligand binding domains. They are believed to be receptors for yet to be identified signaling molecules.

The peroxisome proliferator activated receptors (PPARs) represent a subfamily of structurally related nuclear receptors. Three subtypes have been described: PPARα, γ, and δ. The DNA recognition sequences for all PPAR subtypes are composed of a directly repeating core-site separated by 1 nucleotide. A common recognition sequence is XXXAGGT-CAXAGGTCA (SEQ ID NO:1), however, the core-site (AGGTCA; SEQ ID NO:2) is variable and may change by one or more nucleotide. To bind DNA, PPARs must heterodimerize with the 9-cis retinoic acid receptor (RXR).

The α subtype of PPAR is expressed at high levels in liver and was originally identified as a molecule that mediates the transcriptional effects of drugs that induce peroxisome proliferation in rodents. In addition, PPARα binds to and regulates transcription of a variety of genes involved in fatty acid degradation (β- and ω-oxidation). Mice lacking functional PPARα exhibit decreased β-oxidation capacity and are incapable of increasing this capacity in response to PPARα ligands). Further, these mice inappropriately accumulate lipid in response to pharmacologic stimuli and develop late-onset obesity. Taken together, these data indicate that PPARα acts as both a sensor and an effector in a feedback loop that induces lipid catabolism in response to fatty acid signals.

In contrast to PPARα, the γ subtype of PPAR plays a critical role in the opposing process of fatty acid storage. PPARγ is expressed at high levels in adipocytes where it has been shown to be critical for adipogenesis. Indeed, forced expression of PPARγ in fibroblasts initiates a transcriptional cascade that leads to the expression of adipocyte-specific genes and ultimately to triglyceride accumulation. This implies that signals which modulate PPARγ activity may serve a primary role in regulatory energy homestasis.

PPARδ is ubiquitously expressed and binds several polyunsaturated fatty acids as well as carbaprostacyclin, a synthetic analog of $PGI_2$. PPARδ has been suggested to contribute to the control of embryo implantation and the inhibitory effects of non-steroidal anti-inflammatory drugs on colon cancer.

That PPARs regulate lipid homeostasis implies that putative PPAR ligands represented endogenous regulators of lipid homeostasis. One ligand for PPARγ has been identified 15-deoxy-$\Delta^{12,14}$-prostaglandin $J_2$ (15d–$J_2$). The thiazolidinedione class of anti-diabetic agents mimic 15d–$J_2$, acting as potent ligands. Moreover, the potency of thiazolidinediones as antidiabetic agents correlates with their in vitro affinity for PPARγ. Forman et al., *Cell* 83:803–812 (1995); Wilson et al., *J. Med. Chem.* 39:665–668 (1996). These data suggest that PPARγ mediates the antidiabetic activity of these compounds.

Several other studies have shown that thiazolidinediones simultaneously promote insulin sensitization and increases in adipose cell number/mass in rodent models of NIDDM. Similarly, a genetic analysis suggested a link between obesity and a lower degree of insulin resistance in humans harboring an activating mutation in the N-terminus PPARγ. Ristow et al., *N. Engl. J. Med.* 339:953–959 (1998). That activation of PPARγ can induce adipogenesis in cell culture as well as promote insulin sensitization in vivo appears paradoxical given the epidemiological studies that link weight gain and obesity to NIDDM. However, like the pharmacologic data in rodents, this genetic data suggests that PPARγ activation dissociates adipogenesis from insulin resistance.

Thiazolidinediones reverse insulin resistance in skeletal muscle, adipose tissue and hepatocytes. Komers and Vrana, *Physiol. Res.* 47(4):215–225 (1998). An increase insulin responsiveness is accompanied by a normalization of a wide range of metabolic abnormalities associated with NIDDM, including elevated levels of glucose, insulin, triglycerides, free fatty acids and LDL-cholesterol. Thiazolidinediones do not promote insulin secretion nor do they act as hypoglycemic agents in non-diabetic animals, implying that PPARγ regulates genes that reverse a critical step in the development of insulin resistance.

Several interesting hypotheses have been proposed to explain what causes insulin resistance and how PPARγ activation reverses this process. Insulin resistance may result from increase in circulating levels of free fatty acids. McGarry, *Science* 258:766–770 (1992). If this is the case, PPARγ activation would be predicted to reverse insulin resistance by promoting an increase in fatty acid storage in adipocyes. However, this does not account for the observation that free fatty acids are not elevated in all diabetic models and that a lowering of fatty acids using other treatments is not sufficient to promote insulin sensitization. Alternatively, Spiegelman and colleagues have suggested that insulin resistance results from an increased production of TNFα in the adipose tissue of diabetics. Uysal et al., *Nature* 389:610–614 (1997). Under this theory, PPARγ ligands act by blocking the TNFα-mediated inhibition of insulin signaling, however this is not consistent with all models of NIDDM. How PPARγ normalizes insulin resistance thus remains unclear.

PPARγ is expressed at high levels in both brown (BAT) and white adipose tissue (WAT). In vivo administration of PPARγ ligands have been shown to increase the size of both fat depots. In principle, therefore, both of these tissues could be involved in regulating insulin responsiveness. Transgenic mice with decreased levels of both BAT and WAT may be made by expressing the diphtheria toxin in these tissues using the adipocyte specific aP2 promoter. Burant et al., *J. Clin. Invest.* 100:2900–2908 (1997). By 8–10 months of age these mice apparently lack subcutaneous or intra-abdominal triglyceride-containing adipose tissue. The loss of triglyceride containing cells was accompanied by a progressive increase in insulin resistance and the development of diabetes. Despite the apparent loss of adipose tissue, administration of thiazolidinediones to these mice still resulted in insulin sensitization. These findings indicate that the antidiabetic action of thiazolidinedione occurs independently of thiazolidinedione-induced increases in adipocyte triglyceride content, and perhaps independent of adipose tissue. Burant et al., *J. Clin. Invest.* 100:2900–2908 (1997). However, this may depend on how adipocyte is defined. It is known that PPARγ is induced early in the course of adipogenesis and that PPARγ expression is required for subsequent activation of the aP2 promoter in adipocytes. This transcriptional cascade is followed by massive triglyceride accumulation. The strategy employed by Graves and colleagues for generation of "fat-free" mice depends on expression of a toxic transgene under control of the fat-specific aP2 promoter. However, since the expression of the toxic transgene in fat requires the presence of PPARγ, these mice should possess adipocyte-precursors which express PPARγ in the atrophic remnants of adipose tissue. Thus, it may be more precise to state that thiazolidinedione action is independent of mature adipose tissue. Previous studies have not been designed to address the issue of whether the antidiabetic effects of thiazolidinediones are mediated by cells of the adipocyte lineage.

PPARγ may also be expressed in skeletal muscle and in the liver but its level of expression is at least 10-fold lower in these tissues than in fat. The analysis of PPARγ expression in skeletal muscle has been complicated by the presence of fat cells that interdigitate among the myocytes. Since PPARγ is expressed at high levels in fat, it is possible that PPARγ transcripts seen on northern blots are derived from the contaminating fat cells. Immunohistochemical assays with PPARγ-specific antibodies have shown that PPARγ is expressed in myocyte nuclei at low levels. Despite the ability of thiazolidinediones to promote glucose uptake sensitization of skeletal muscle in vivo, these compounds had no detectable effect on glucose uptake after a five-hour exposure. Since the antidiabetic effects of thiazolidinediones are observed only after 1–2 weeks of treatment, a longer duration of exposure may be required to elicit the antidiabetic response, however it is difficult to maintain phenotypic myocytes in culture for this length of time. For similar reasons, it is not clear whether the liver is a direct target for the antidiabetic effects of thiazolidinediones.

"Knockout" mice lacking the PPARγ gene have an embryonic lethal phenotype. Thus, these mice are not useful in studying the effects of PPARγ in the adult animal. In principle, it might be possible to bypass the embryonic lethal phenotype by generating tissue-specific knockouts of PPARγ. In practice, this approach has been complicated by the need to express sufficient quantities of the cre-recombinase in the target tissue. Assuming these technical difficulties can be overcome, the resulting mice would be useful in an analysis of the physiological consequences resulting from the loss of PPARγ function. In any case, these mice would not be useful to study the consequences of PPARγ activation. A method of studying what the effects would be in individual tissues upon activation of PPARγ by a drug, or the like would be enormously useful.

Numerous screening approaches have been established to identify ligands (agonists and antagonists) for PPARγ. All rely on the observation that the affinity of ligand binding to nuclear receptors is determined by the receptor itself, or by a nuclear receptor dimer. Such screening methods do not take into consideration any other factors which may affect the affinity of PPARγ for its ligands, either qualitatively or quantitatively, in vivo. Therefore, a screening method which is aimed at discovering novel PPARγ ligands under different conditions which mimics more closely some in vivo conditions would be very useful.

SUMMARY OF THE INVENTION

Accordingly, this invention provides a method of identifying nuclear receptor controlled genes in a specific tissue of an animal, which comprises providing an expression vector containing a constitutively active nuclear receptor gene which is fused at the N-terminus to the transcriptional activation domain of the Herpes viral VP126 protein, and is linked to a promoter element which drives tissue-specific expression, transferring the constitutively active nuclear receptor gene to the animal, expressing the constitutively active nuclear receptor gene in the animal, determining the level of expression of candidate target genes of the nuclear receptor in the tissue, and identifying genes which exhibit altered expression.

In another embodiment, the invention provides a method of modulating the in vivo expression of nuclear receptor controlled genes in a specific tissue of an animal, which comprises providing an expression vector containing a constitutively active nuclear receptor gene which is fused at the N-terminus to the transcriptional activation domain of the Herpes viral VP126 protein, and is linked to a promoter element which drives tissue-specific expression, transferring the constitutively active nuclear receptor gene to the animal, and expressing the constitutively active nuclear receptor gene in vivo in the animal.

In yet another embodiment, the invention provides a transgenic non-human animal harboring a constitutively active nuclear receptor gene which is fused at the N-terminus to the transcriptional activation domain of the Herpes viral VP126 protein, and is linked to a promoter element which drives tissue-specific expression.

In yet a further embodiment, the invention provides a method of screening for compounds which bind to PPARγ which comprises including a coactivation protein PBP, and an improvement to a method for screening for compounds which bind to PPARγ which comprises including PBP during binding of ligands to PPARγ.

DETAILED DESCRIPTION OF THE INVENTION

Figure 1:
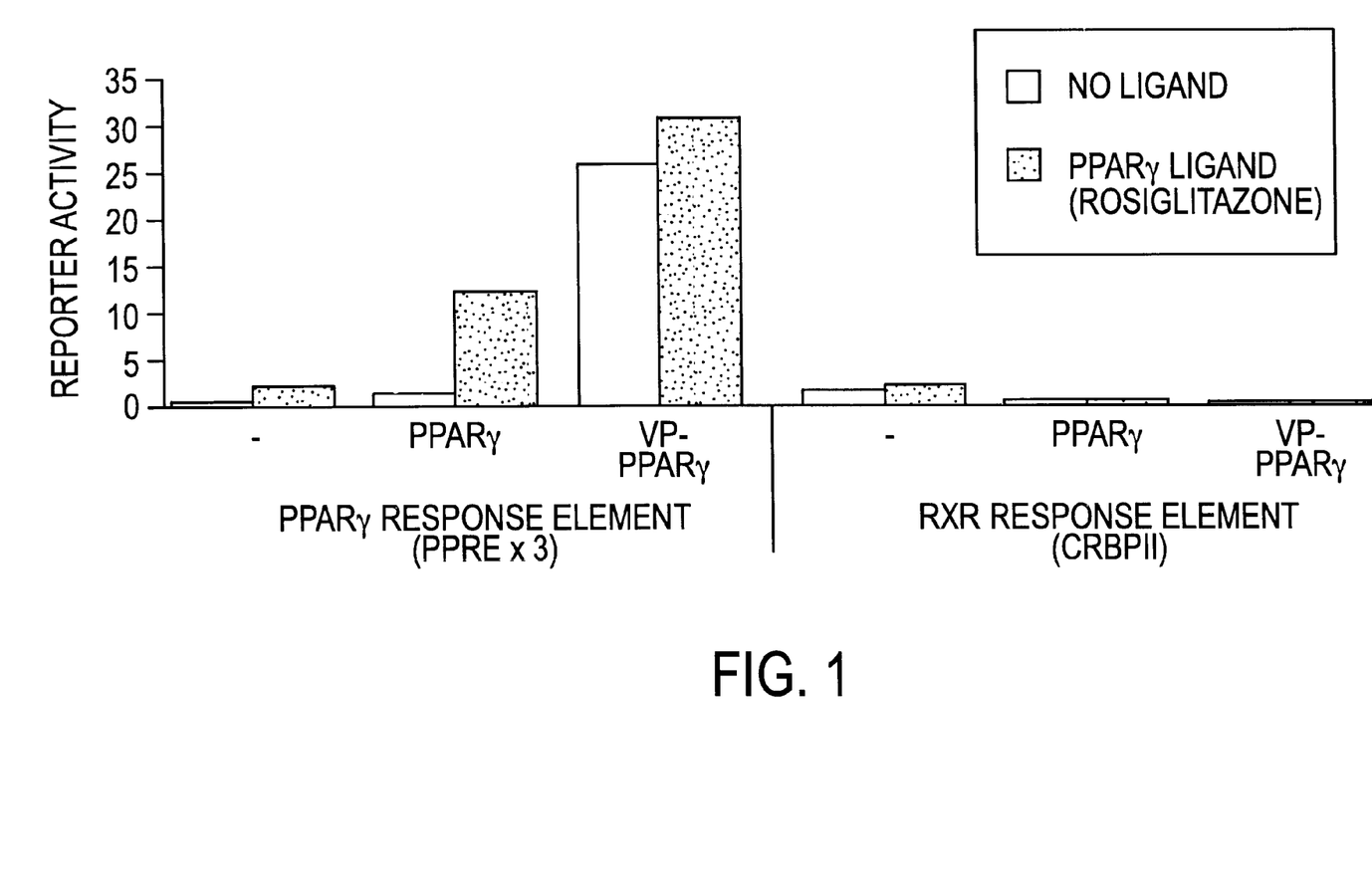
FIG. 1 is a histogram depicting reporter-activity of PPARγ and VP-PPARγ.
Figure 2A:
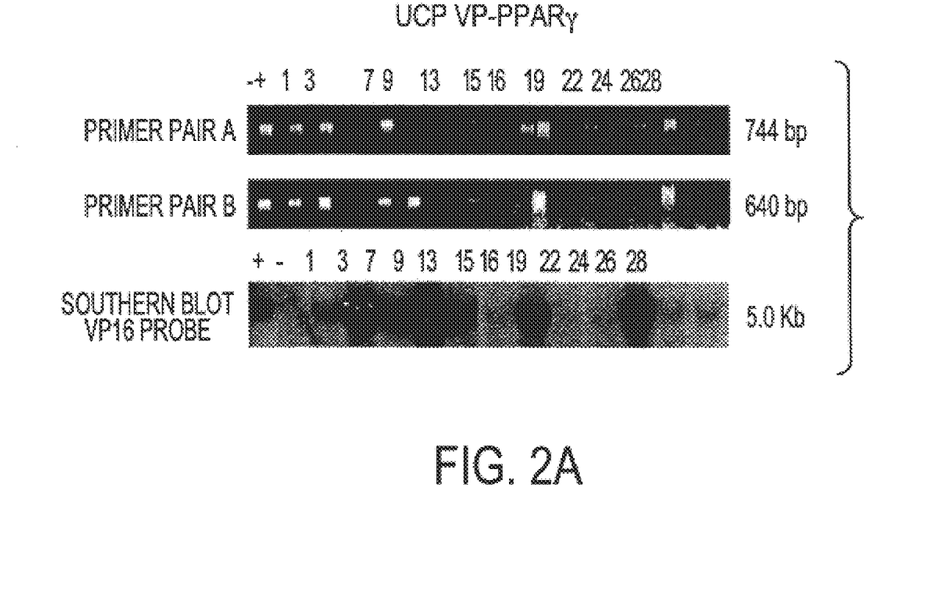
FIGS. 2A–2D show which animals contain the indicated exogenous VP-PPARγ gene by RT-PCR using two primer pairs with confirmation by Southern blot.
Figure 2B:
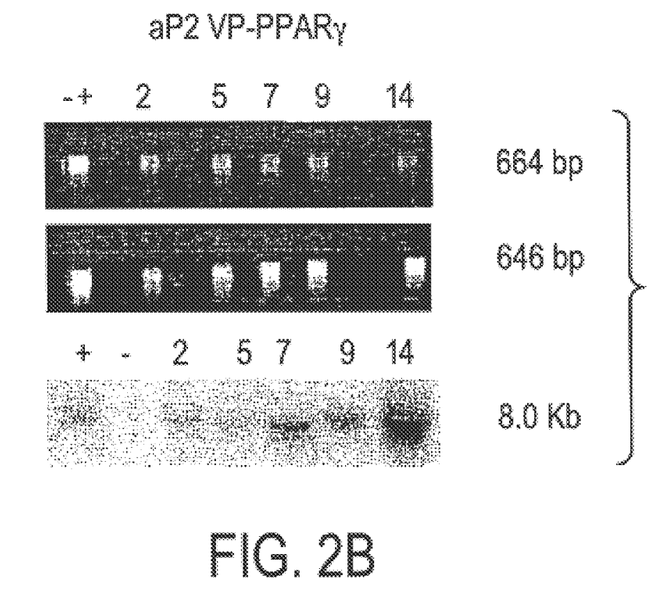
Figure 2C:
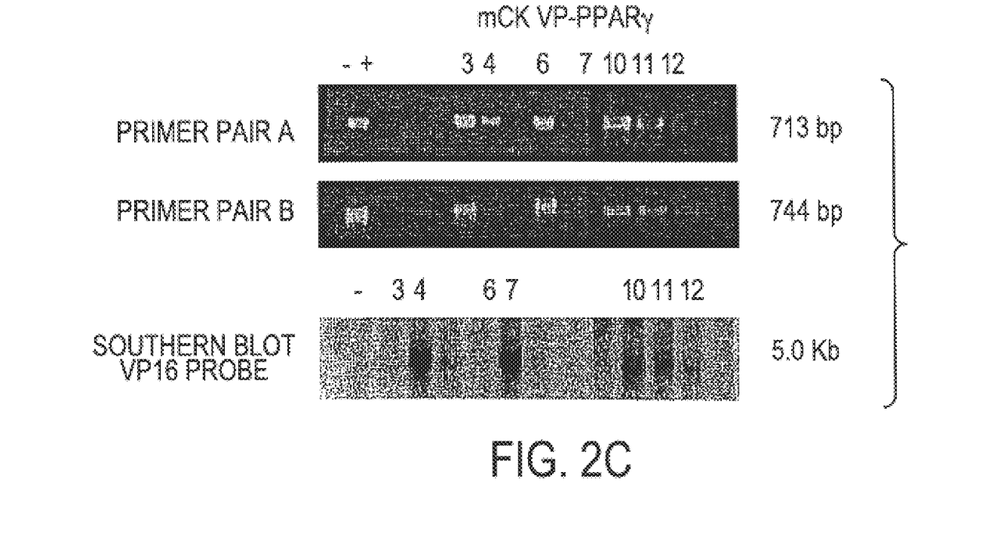
Figure 2D:
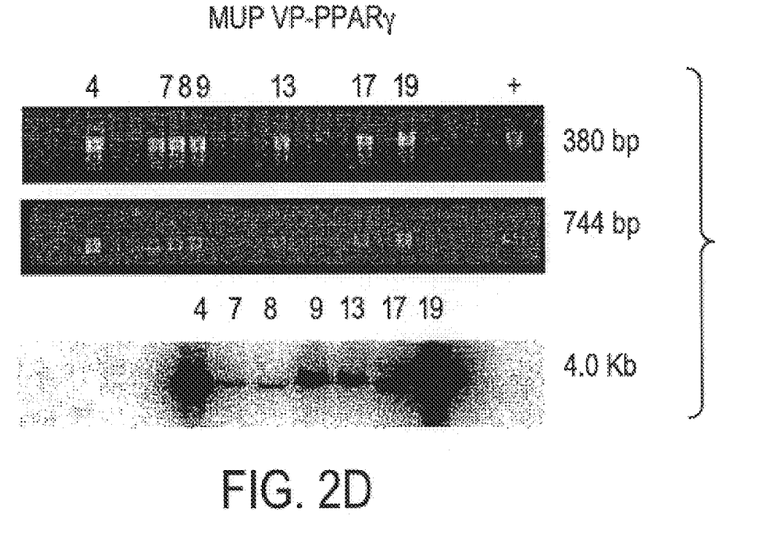

A constitutively active form of PPARγ was generated by fusing the transcriptional activation domain of the Herpes viral VP126 protein to the N-terminus of PPARγ (VP-PPARγ). N-terminus fusions were created as this does not alter the DNA binding or dimerization activity of receptors. The VP16 transactivation domain was chosen because it is well characterized and is known to function independent of nuclear receptor ligands. Recent studies indicate that VP16 recruits a transcription activation complex that is indistinguishable from that utilized by PPARγ and other nuclear receptors. The altered receptor activated transcription via PPARγ response elements in the absence of ligand, yet has similar DNA binding and transactivation specificity as the wild-type receptor. As shown in FIG. 1, the VP-PPARγ chimera activates PPARγ response elements in the absence of ligand but has no effect on non-PPARγ response elements including a closely related DR-1 type response element (CRBPII) specific for RXR homodimers.

To further confirm the biological activity of VP-PPARγ, this receptor was tested for induction of adipocyte differentiation in the absence of PPARγ ligands using the adipogenic system established by Tontonoz and Spiegelman. Tontonoz and Spiegelman, *Cell* 79:1147–1156 (1994). The NIH 3T3 cells in this system lack PPARγ and thus cannot differentiate into adipocytes. However, when infected with PPARγ-expressing retroviruses, these cells will undergo adipocyte differentiation in the presence of PPARγ ligands. VP-PPARγ was cloned into a replication defective retroviral expression vector (pBABE). Expression of the wild-type receptor in NIH-3T3 cells resulted in cells that underwent nearly 100% differentiation in response to PPARγ ligands. In contrast, the VP-PPARγ expressing retroviruses led to an equally efficient adipocyte conversion in the absence of PPARγ ligand (data not shown). These results are consistent with the transfection studies and confirm that VP-PPARγ acts as a constitutively active form of VP-PPARγ in a biologically relevant system.

Transgenic expression vectors that would specifically direct expression of this chimera to the BAT, WAT, skeletal muscle and liver of transgenic mice were then constructed. The transgenic expression vectors contained VP-PPARγ linked to the following promoter elements which are known to drive tissue-specific expression: creatine kinase in skeletal muscle (Moller et al. *Endocrinol.* 137:2397–2405 (1996)); major urinary protein in liver (Held et al. *EMBO J.* 8:183–191 (1989)); aP2 in total adipose tissue (Ross et al., *Genes Dev.* 7:1318–1324 (1993)); and uncoupling protein 1 in brown adipose tissue (Lowell et al., *Nature* 336:740–742 (1993)). The tissue specificity of these promoters have been well documented and they are transcribed very late in fetal development or within a few weeks after birth. Thus, this method allows expression of the chimeric receptor in a tissue and temporal-specific manner that avoids the potential problem of developmental defects resulting from transgenic expression.

The transgenes described above were injected into zygotes derived from C57BL/KsJ mice. These mice are known to be genetically susceptible to the development of NIDDM. After birth, the transgenic mice were screened for integration of the transgene using two different sets of PCRT primers. Positive mice were confirmed by Southern blot analysis using a VP16 probe that specifically recognizes the transgene. For each promoter construct, several founders were identified that have incorporated an apparently intact transgene (FIG. 2). The founder mice were screened for tissue specific expression of PPARγ-specific probes. Levels of expressed chimeric protein will be determined by western blot analysis using a monoclonal antibody (12CA5) that specifically recognizes a 9 amino acid epitope tag engineered into the original VP-PPARγ chimera.

To confirm the functionality of the transgene, levels of expression of several known PPARγ target genes (e.g., UCP, aP2 ) were measured. Elevated levels of expression of these target genes would be expected in transgenic animals that express a functional VP-PPARγ. Different lines of mice expressing VP-PPARγ were selected for each promoter construct. These mice have been analyzed by RT-PCR and the results indicate that the transgenes show the expected pattern of expression. For example, the mice containing the VP-PPARγ transgene expressed the transgene in brown fat but not in white fat, liver, skeletal muscle or other tissues that were examined. Colonies of the mice were expanded for the analyses described below.

A cursory phenotypic analysis of the mice suggests that the transgenes are appropriately expressed. Specifically, the UCP-VP-PPARγ mice would be expected to be expressed uniquely in brown fat and to lend to an overproduction of uncoupling protein 1. Tai et al., *J. Biol. Chem.* 271:29909–29914 (1996). As UCP-1 activity is associated with the burning of fat, these mice might be expected to have decreased white adipose stores. By 20 weeks of age, the UCP-VP-PPARγ founders weighed 17% less than their control littermates and had considerably less white adipose tissue (data not shown).

Figure 3:
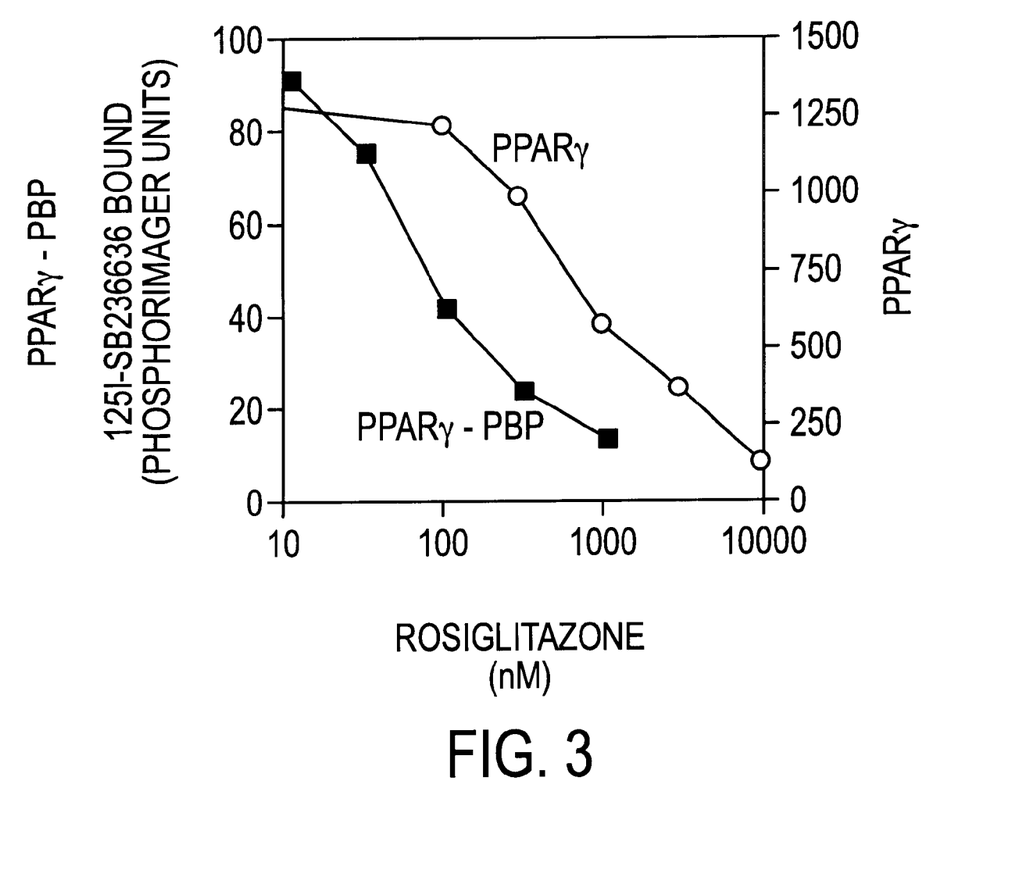
FIG. 3 presents displacement curves demonstrating that the affinity of PPARγ for its ligand is increased by the coactivator PBP.

We now show that in affinity of PPARγ for its ligands is modulated by other factors. In particular, the ligand binding affinity is determined by interaction of the receptor with a coactivator protein such as PBP (Unigene # Hs. 15589). The affinity of PPARγ for rosiglitazone was measured in the absence or presence of PBP (FIG. 3). Binding to PPARγ (without PBP) was determined by measuring the displacement of a radioactive ligand [$^{125}$I]SB-236636 according to the methods of Young et al., J. Pharm. Exp. Ther. 284(2): 751–759, 1998. As seen in FIG. 3 (O), half-maximal displacement of [$^{125}$I]SB-236636 occurred at rosiglitazone concentrations of 1000 nM. However, this compound is known to act in cells with half-maximal activity at concentrations of approximately 50 nM. See Forman et al., Cell 83(5): 803812, 1995; Kliewer et al., Cell 83(5):813–819, 1995. Nuclear receptors activate transcription by recruiting coactivator proteins, therefore whether the affinity of PPARγ for rosiglitazone was increased in the presence of the coactivator PBP was examined. Specifically, the displacement of [$^{125}$I]SB-236636 by rosiglitazone was measured after formation of a PPARγ-RXR DNA complex in the presence or absence of PBP. Complexes were separated by electrophoresis through a non-denaturing gel and the amount of [$^{125}$I] SB-236636 in the complex was determined by phosphorimager analysis. As seen in FIG. 3 (■), half-maximal displacement of the PPARγ-RXR-DNA-PBP complex was observed at a concentration of about 50 nM. PBP binding resulted in an approximately 20-fold increase in the affinity of PPARγ for its ligand. The enhanced binding affinity is similar to the observed potency in cells.

As PPARγ ligands are being used for or suggested as treatments for a variety of diseases, these data indicate that screening strategies aimed at discovering novel ligands for the treatment of such diseases should utilize a complex containing both PPARγ and PBP or PPARγ and another coactivator protein. In addition to the approach described above, it is understood that a variety of alternative methodologies are available to screen these complexes for their ability to interact with ligand. Moreover, it is anticipated that similar strategies might be applicable to other receptors in addition to PPARγ.

One assay for screening ligands for their ability to activate pPPARγ may be performed in CV-1 cells transfected with PPARγ, a suitable reporter gene and the coactivator protein PBP. For example, cells transfected with and transiently expressing PPREx3 (reporter gene, three copies), PPARγ and PBP may be used to screen different compounds for activation of the PPARγ gene. Methods for assays of this type which are suitable for use with this invention include the methods of Forman et al., Cell 83:803–812, 1995 and Forman et al., Proc. Natl. Acad. Sci. 94:4312–4317, 1997, the disclosures of which are hereby incorporated by reference. Assays described for PPARα and PPARδ as well as PPARγ may be used or modified by those of skill in the art using the disclosures of this specification as a guide.

The following non-limiting example is included to illustrate the invention.

EXAMPLE 1

Ligand Binding Assay

Ligand binding assays are performed with a GST-mPPARγ1 fusion protein that is expressed E. coli and purified by affinity chromatography on glutathione-Sepharose beads. Following elution with glutathione, the purified protein is extensively dialyzed, and the GST moiety is cleared away with thrombin. The GST protein then is removed by a second round of glutathione-Sephanose chromatography followed by extensive dialysis. Ligand binding assays are performed by incubating PPARγ and [$^3$H] BRL49653 (31 Ci/mmol) in a buffer containing 10 mM Tris (pH 8.0), 50 mM Kcl, 10 mM DDT and PBP. Competitor ligands or solvent carriers also may be added. Binding reactions are incubated for 30 minutes at 25° C. and then chilled to 4° C. for 15 minutes. Free and bound ligand are separated using a spin column containing a suspension of Sephadex G-25 (Sigma) in 15% glycerol, 25 mM Tris (pH 7.8), 0.05% Triton X-100, 0.5 mM EDTA and 75 mM KCl. The amount of bound [$^3$H]BRL49653 is determined by liquid scintillation counting.

REFERENCES

The disclosures of the references listed below are hereby incorporated by reference.

1. Olefsky, "Treatment of insulin resistance with peroxisome proliferator-activated receptor gamma agonists." J. Clin. Invest. 2000 August;106(4):467–72.
2. Dussault and Forman, "Prostaglandins and fatty acids regulate transcriptional signaling via the peroxisome proliferator activated receptor nuclear receptors." Prostaglandins Other Lipid Mediat. 2000 June;62(1):1–13.
3. Buchan and Hassall, "PPAR agonists as direct modulators of the vessel wall in cardiovascular disease." Med. Res. Rev. 2000 September;20(5):350–66.
4. Kersten et al., "Roles of PPARs in health and disease." Nature 2000 May 25;405(6785);421–4.
5. Rosen et al., "Transcriptional regulation of adipogenesis." Genes Dev. 2000 June 1;14(11):1293–307.
6. Gervois et al., "Regulation of lipid and liporprotein metabolism by PPAR activators." Clin. Chem. Lab. Med. 2000 January;38(1):3–11.
7. Wu, "A nuclear receptor to prevent colon cancer." N. Engl. J. Med. 2000 March 2:342(9):651–3.
8. Bishop-Bailey, "Peroxisome proliferator-activated receptors in the cardiovascular system." Br. J. Pharmacol. 2000 March;129(50):823–34.
9. Willson et al., "The PPARs: from orphan receptors to drug discovery." J. Med. Chem. 2000 February 24;43(4):527–50.
10. Tontonoz and Nagy, "Regulation of macrophage gene expression by peroxisome-proliferator-activated receptor gamma: implications for cardiovascular disease." Curr. Opin. Lipidol. 1999 December; 10(6):485–90.
11. Young et al., "Identification of high-affinity binding sites for the insulin sensitizer rosiglitazone (BRL-49653) in rodent and human adipocytes using a radioiodinated ligand for peroxisomal proliferator-activated receptor gamma." J. Pharmacol. Exp. Ther. 1998 February;284(2):751–9.
12. Forman et al., "15-Deoxy-delta 12, 14-prostaglandin J2 is a ligand for the adipocyte determination factor PPAR-gamma." Cell Dec. 1, 1995;83(5):803–12.
13. Kliewer et al., "A prostaglandin J2 metabolite binds peroxisome proliferator-activated receptor gamma and promotes adipocyte differentiation." Cell Dec. 1, 1995;83 (5):813–9.

What is claimed is:

1. A method of screening for compounds that bind to a complex of peroxisome proliferator activated receptor gamma (PPARγ) and PPARγ binding protein (PBP), which comprises:
  (a) incubating a PPARγ-PBP complex with a labeled candidate ligand compound, wherein detectable endogenous PPARγ ligand is not present; and
  (b) determining whether said labeled candidate ligand compound has bound to said PPARγ-PBP complex.

2. The method according to claim 1 wherein an exogenous PPARγ ligand is present during step (a).

3. The method according to claim 2 wherein said exogenous PPARγ ligand is rosiglitazone.

* * * * *